United States Patent
Newcombe et al.

(10) Patent No.: US 8,268,011 B2
(45) Date of Patent: Sep. 18, 2012

(54) PROSTHETIC LIMB ATTACHMENT

(75) Inventors: Lindsay K. Newcombe, London (GB); Michael E. Dewar, Somerset (GB)

(73) Assignee: University College London, London (GB)

( * ) Notice: Subject to any disclaimer, the term of this patent is extended or adjusted under 35 U.S.C. 154(b) by 353 days.

(21) Appl. No.: 10/590,581

(22) PCT Filed: Mar. 9, 2005

(86) PCT No.: PCT/GB2005/000892
§ 371 (c)(1),
(2), (4) Date: Jun. 15, 2007

(87) PCT Pub. No.: WO2005/087145
PCT Pub. Date: Sep. 22, 2005

(65) Prior Publication Data
US 2008/0058957 A1    Mar. 6, 2008

(30) Foreign Application Priority Data

Mar. 12, 2004    (GB) .................................... 0405530.7

(51) Int. Cl.
*A61F 2/78* (2006.01)
(52) U.S. Cl. ......................................................... 623/32
(58) Field of Classification Search .................... 623/32, 623/38
See application file for complete search history.

(56) References Cited

U.S. PATENT DOCUMENTS

| | | | |
|---|---|---|---|
| 2,784,416 A * | 3/1957 | Goodwin et al. ............... | 623/59 |
| 3,947,897 A | 4/1976 | Owens et al. | |
| 4,158,895 A | 6/1979 | Bright et al. | |
| 4,186,449 A * | 2/1980 | Horvath .......................... | 623/27 |
| 4,516,442 A * | 5/1985 | Davis .............................. | 74/529 |
| 5,226,918 A * | 7/1993 | Silagy et al. .................... | 623/32 |
| 5,314,500 A * | 5/1994 | Weddendorf .................... | 623/57 |
| 5,425,781 A * | 6/1995 | Allard et al. .................... | 623/38 |
| 5,545,230 A * | 8/1996 | Kinsinger et al. .............. | 623/38 |
| 5,746,773 A * | 5/1998 | Littig .............................. | 623/35 |
| 5,913,901 A * | 6/1999 | Lacroix ........................... | 623/47 |
| 5,928,290 A * | 7/1999 | Gramnas ......................... | 623/33 |
| 6,106,559 A * | 8/2000 | Meyer ............................. | 623/33 |
| 6,302,918 B1 * | 10/2001 | Gramnas ......................... | 623/27 |
| 6,352,560 B1 * | 3/2002 | Poeschmann et al. ........ | 623/23.4 |
| 6,425,925 B1 | 7/2002 | Grundei | |
| 6,436,149 B1 * | 8/2002 | Rincoe ............................ | 623/47 |
| 6,451,058 B2 * | 9/2002 | Tuke et al. ................. | 623/22.21 |
| 6,565,156 B1 * | 5/2003 | Yamashita et al. ........ | 297/354.12 |
| 6,589,288 B2 * | 7/2003 | McDowell et al. ............. | 623/33 |

(Continued)

FOREIGN PATENT DOCUMENTS

DE    196 50 816 A1    6/1998

(Continued)

*Primary Examiner* — Bruce E Snow
(74) *Attorney, Agent, or Firm* — Carmen Patti Law Group, LLC

(57) ABSTRACT

The present invention provides an apparatus (1) for attaching a prosthetic limb to the bone of a patient, the apparatus comprising a proximal component (2) to mount to a bone implant, a distal component (3) to mount to a prosthetic limb, and a coupling body (4, 5) coupling together the proximal and distal components (2,3) with freedom to articulate when, in use, a bending and/or torsional force is applied to the prosthetic limb, only when the force exceeds a threshold level, whereby the force may be accommodated by articulation within the attachment apparatus (1). The attachment apparatus (1) thus functions as a fail-safe articulation mechanism protecting the bone of the patient.

14 Claims, 4 Drawing Sheets

U.S. PATENT DOCUMENTS

| | | | |
|---|---|---|---|
| 6,605,118 B2 * | 8/2003 | Capper et al. | 623/36 |
| 6,626,951 B1 * | 9/2003 | Gramnas | 623/33 |
| 6,893,468 B2 * | 5/2005 | Lund | 623/36 |
| 6,942,485 B1 | 9/2005 | Richard | |
| 7,081,138 B2 * | 7/2006 | Hellberg | 623/36 |
| 7,083,654 B2 * | 8/2006 | Helenberger et al. | 623/33 |
| 7,108,722 B2 * | 9/2006 | Wagman | 623/38 |
| 2002/0103544 A1 | 8/2002 | McDowell et al. | |
| 2002/0116071 A1 | 8/2002 | Slemker et al. | |
| 2003/0236575 A1 | 12/2003 | Yu et al. | |
| 2004/0030410 A1 * | 2/2004 | Wagman | 623/27 |
| 2004/0102856 A1 * | 5/2004 | Hellberg | 623/33 |
| 2005/0027371 A1 * | 2/2005 | Chen | 623/38 |
| 2005/0038522 A1 * | 2/2005 | Helenberger et al. | 623/36 |

FOREIGN PATENT DOCUMENTS

| | | |
|---|---|---|
| DE | 199 32 388 C1 | 12/2000 |
| DE | 102 47 397 B3 | 1/2004 |
| EP | 1 378 215 A1 | 1/2004 |

* cited by examiner

PROSTHETIC LIMB ATTACHMENT

FIELD OF THE INVENTION

The present invention concerns improvements in and relating to prosthetic limb attachment.

BACKGROUND OF THE INVENTION

In recent years procedures have been developed in which a limb prosthesis (artificial arm or leg) is attached by a bone implant directly to the bone of an amputee's residual limb. As an example of such a procedure, the present applicant's own UK patent application GB-A-2,365,355 describes and illustrates the use of an intra-osseous transcutaneous implant that is secured at a distal end to a limb prosthesis or severed limb and that attaches at a proximal end directly to the bone of the patient's residual limb through the skin. The implant is differentially surface treated, having coatings (e.g. of hydroxy apatite and/or a protein such as laminin or fibronectin to encourage fibrous in-growth) at its proximal end to promote optimal integration with the bone, ligament and skin tissues of the residual limb while having a very low surface energy at its distal (external) end deterring bacterial colonisation at the implant's external skin interface.

The transcutaneous bone implants of GB-A-2,365,355 are relatively securely held in place to the patient's native tissue and are less prone to infection than prior transcutaneous implants. However, in use of these or other direct bone implants for attachment, the attachment can still pose mechanical problems in use. In particular, the joint of the prosthesis to the bone generally has no give and there is a substantial risk that a bending or torsional force applied to the prosthetic limb may either break the bone or cause the bone implant to become detached from it.

The present invention seeks, amongst other objectives, to provide means for addressing the shortcomings of the existing attachments and the bone implant differential coating technology of GB-A-2,365,355 suitably is used in combination with the present invention.

SUMMARY OF THE INVENTION

According to a first aspect of the present invention there is provided an apparatus for attaching a prosthetic limb to the bone of a patient, the apparatus comprising:
  i) a proximal component to mount to a bone implant;
  ii) a distal component to mount to a prosthetic limb; and
  iii) a coupling body coupling together the proximal and distal components with freedom to articulate when, in use, a bending and/or torsional force is applied to the prosthetic limb only when the force exceeds a threshold level whereby the force may be accommodated by articulation within the attachment apparatus.

The attachment apparatus thus functions as a fail-safe articulation mechanism protecting the bone of the patient. Suitably it is first attached to the bone implant component and then has the prosthetic limb attached to it. However, it may be incorporated into the bone implant component or the prosthetic limb and may be, in part or wholly, integrally formed or assembled with the bone implant or the limb prosthesis.

Preferably the coupling body has a clutch mechanism to rotationally couple the prosthetic limb to the bone implant in use but which automatically disengages, rotationally decoupling the prosthetic limb from the bone implant, when torque applied to the prosthetic limb exceeds a predetermined threshold.

The apparatus suitably has a resilient biasing means whereby the clutch mechanism is resiliently biased to the rotationally coupled state and whereof the biasing force applied to the clutch mechanism by the resilient biasing means in use determines the threshold level of torque on the prosthetic limb that will cause disengagement of the clutch mechanism.

Preferably the apparatus has adjustment means whereby the threshold level of torque on the prosthetic limb that will cause disengagement of the clutch mechanism may be increased or decreased. In the case that the apparatus has the aforesaid resilient biasing means, the adjustment means may comprise a screw adjustment means 35 that suitably is screw-threadedly adjustable axially toward or away from the clutch mechanism.

Preferably the clutch mechanism has opposing sets of co-operating clutch teeth whereof the teeth are substantially symmetrical in profile whereby the clutch mechanism may be disengaged in either rotational direction of torque, clock-wise or anti-clockwise, applied to the prosthetic limb.

Suitably the clutch mechanism is on the proximal component. This is particularly useful when used in tandem with an automatically disengageable connector to allow tilting, since it will remain effectively operable even when the tilting connector is actuated to tilt. Preferably it is configured to be located external to the patient's skin in use so that there will be no tearing of the patient's skin when the clutch mechanism disengages.

Preferably the coupling body has an automatically disengageable connector that couples together the proximal and distal components so that one is in a fixed angle relation to the other (e.g. axially aligned with or at a fixed angle of incline to the axis of the other) in normal use but with freedom to articulate away from the fixed angle relation when, in use, a bending force is applied to the prosthetic limb only when the force exceeds a threshold level.

The apparatus with disengageable connector suitably has a resilient biasing means whereby the disengageable connector is resiliently biased to the coupled state and whereof the biasing force applied to the disengageable connector by the resilient biasing means in use determines the threshold level of bending force on the prosthetic limb that will cause disengagement of the disengageable connector.

Preferably the disengageable connector comprises a pin mounted to one of the proximal and distal components and co-operating with a socket in the other of the proximal and distal components. Suitably the pin is mounted to be movable back and forth axially of the component to which it is mounted and biased forwardly. Preferably the pin is concentrically mounted within the component.

Preferably the pin has a domed (e.g. ball-shaped) or pointed tip and the socket is of a corresponding concave shape whereby a bending force applied to the prosthetic limb in use will cause the tip of the pin to ride outwardly up the socket wall.

Suitably the shape of the tip is domed or substantially conical to facilitate disengagement of the disengageable connector whichever radial orientation the bending force is applied from. Preferably such an arrangement is combined with the disengageable connector being configured to allow universal articulation, substantially in the manner of a ball joint, when it disengages.

In one preferred embodiment the disengageable connector comprises a T-shaped formation at the end of one or both of the proximal and distal components that are adjacent each other, the head of the or each T-shaped formation being curved/arcuate to facilitate tilting of one component relative to the other. Suitably the T-shaped formations substantially nest one against the other and suitably they are accommodated in the coupling body or a further coupling body, to tilt within the coupling body. Amongst special benefits from the use of a disengageable connector of this type in contrast to, say, a ball-in-socket connector, is that the fulcrum about which the distal component tilts is better distanced from the bone implant, further reducing risk of trauma to that area.

Preferably the coupling body has slots therethrough, through each of which a respective end of a head of a T-shaped formation extends and whereby the end may protrude to a greater or lesser extent as the component tilts, whereby the coupling body provides a captive articulated joint with a restricted degree of tilting freedom of movement.

Suitably one T-shaped formation is oriented in the coupling body with its head substantially orthogonal to the head of the other, whereby through tilting of each relative to the other an approximately universal or gyrating articulation may be achieved.

Preferably a coupling part of the apparatus further comprises a shear pin means whereby the apparatus will uncouple at the coupling part through shearing of the shear pin means if an excess tensile/distracting force is applied to it. Suitably the coupling part here is formed at or in the proximal component and the shear pin is demountable or retractable whereby the apparatus and prosthesis conveniently may be demounted by the user while the main part of the apparatus and prosthesis remain coupled to each other. Thus the shear pin may serve a dual function, allowing daily mounting and demounting of the prosthesis and failsafe assembly while providing for tensile force failsafe.

BRIEF DESCRIPTION OF THE DRAWINGS

A preferred embodiment of the present invention will now be more particularly described, by way of example, with reference to the accompanying drawings, wherein.

DESCRIPTION OF THE PREFERRED EMBODIMENT

Figure 1:
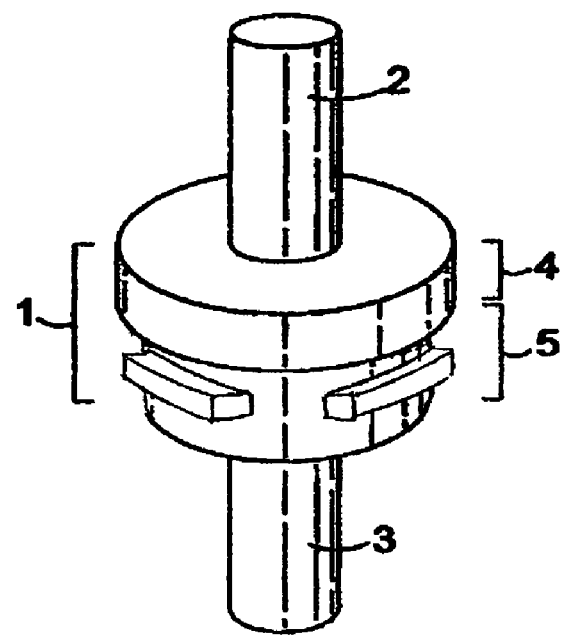
FIG. 1 is a schematic perspective view of the attachment apparatus of the preferred embodiment.

An overall view of the attachment apparatus is shown in FIG. 1. The attachment apparatus 1 is approximately cylindrical in shape with an elongate proximal component 2 at the proximal end that attaches to the bone implant and an elongate distal component 3 at the distal end to which the prosthetic limb is attached. (In the figures these two components are also shown as cylindrical for convenience, but in practice they may not necessarily be so.)

The apparatus 1 has two movement accommodating mechanisms: one to allow the prosthetic limb to tilt away from axial alignment (or other fixed angle relationship) with the bone implant/residual limb when excessively forced and the other to allow twisting/axial rotation of the prosthetic limb without twisting/rotating the bone implant when excessive torque is applied. The twisting/axial rotation accommodating feature is suitably provided in a clutch unit 4 on the proximal component 2 while the tilting feature 5 is at the interface of the proximal component 2 and distal component 3.

Figure 2:
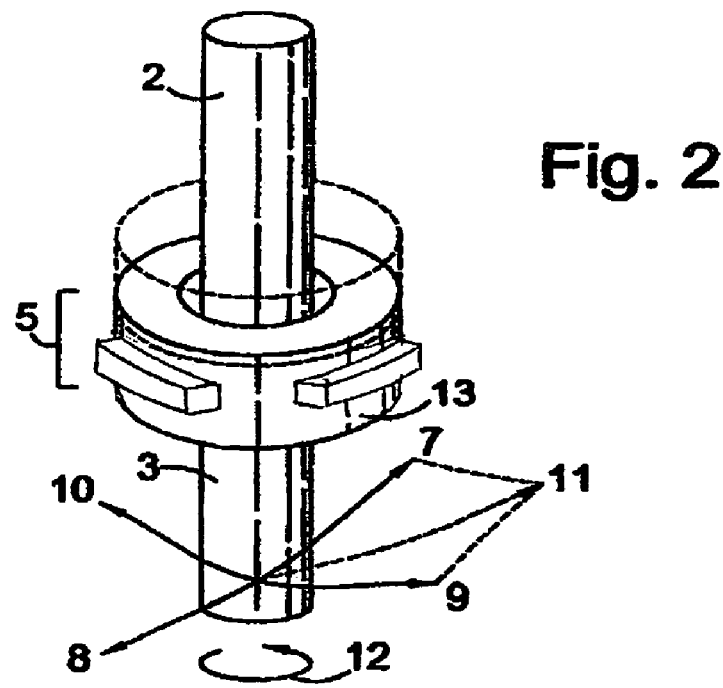
FIG. 2 is a view similar to FIG. 1 but with a clutch mechanism part omitted to show the parts of the attachment responsible for bending articulation.

An overall view of the bending/tilting feature 5 is shown in FIG. 2. Starting from the position when the proximal and distal components 2 and 3 are in-line the mechanism allows the distal component 3 to tilt in four directions, 7 or 8 and 9 or 10, relative to proximal component 2. By a combination of these movements distal component 3 can therefore tilt (gyrate) in any direction (e.g. 11 is a combination of 7 and 9) without being able to rotate 12 about its own axis. Although in practice it is tilting of distal component 3 relative to proximal component 2 that is significant in terms of the operation of the device, for descriptive purposes it is easier to consider the movement of the components 2, 3 relative to coupling body 13 that couples the components 2, 3 together.

Figure 3:
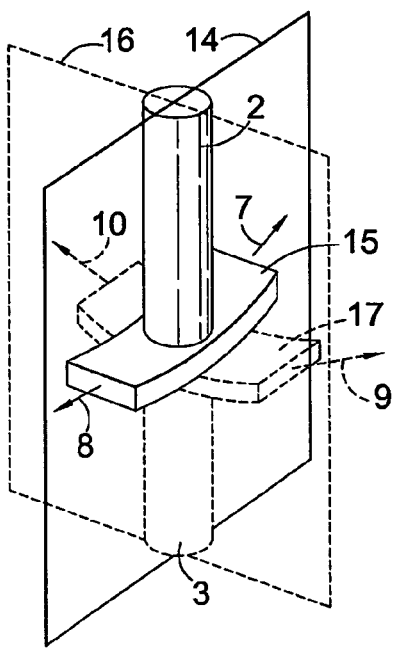
FIG. 3 is a view similar to FIG. 2 but with a connector body of the attachment removed to show the co-operating ends of the proximal and distal components and how they may move relative to each other.

In FIG. 3 the coupling body 13 of the mechanism has been omitted to show the operation of the device. Relative to the body 13 (not shown in FIG. 3) the proximal element 2 is constrained to rotate/tilt only in directions 7 or 8, i.e. in the plane 14, by the curved element 15. The distal element 3 is similarly constrained to rotate/tilt only in directions 9 or 10, i.e. in the plane 16 which is orthogonal to plane 14, by the curved element 17.

Figure 4:
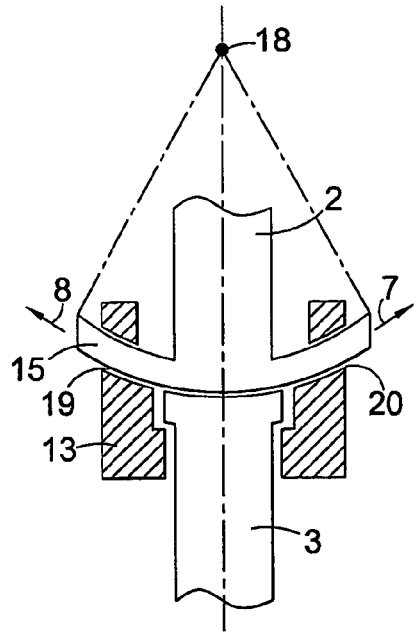
FIG. 4 is a schematic section through the apparatus taken in plane 14 in FIG. 3.

FIG. 4 is a section through the tilting mechanism in the plane 14. The centre of rotation of the proximal element 2 is located at a point 18 proximal to the mechanism. The location of point 18 is determined by the curvature of the element 15. Element 15 is constrained to move in an arc about the centre 18 by shaped slots 19 and 20 in the body of the mechanism 13.

Figure 5:
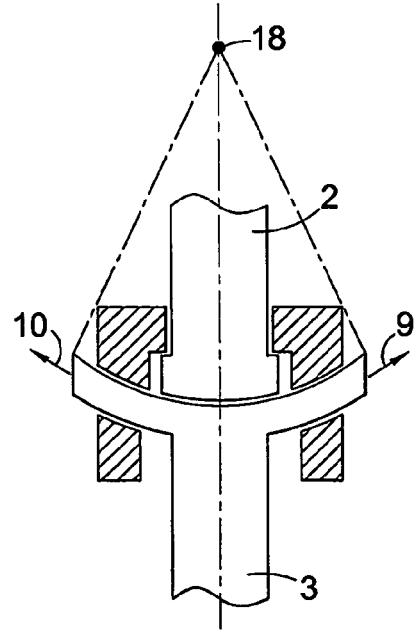
FIG. 5 is a schematic section through the apparatus taken in plane 16 in FIG. 3.

FIG. 5 is a section through the mechanism in the plane 16. In an identical manner to that for the proximal element 2, the distal element 3 is constrained to rotate about the centre of rotation 18. Because the curved element 17 is situated distal to the curved element 15 its radius of curvature is greater than that of element 15 so that the centres of rotation are coincident at point 18.

Figures 6, 6A:
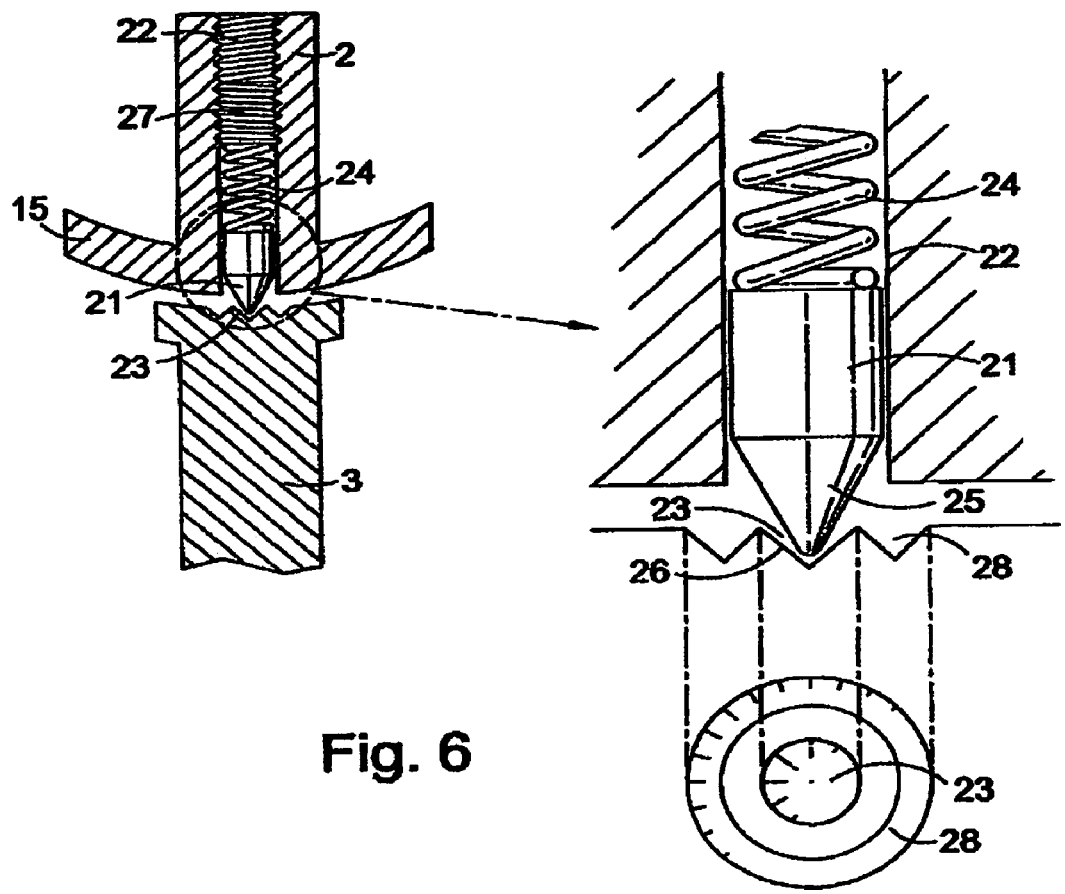
FIG. 6 is a detail section corresponding to FIG. 4 but showing the latching detail of the coupling that resists bending at the coupling until excessive force is applied.
FIG. 6A is a close-up view of the latching detail in FIG. 6.

In the normal situation the elements 2 and 3 are prevented from moving relative to each other by the latching mechanism shown in FIG. 6. A pin, here shown as a cylindrical element 21 which is free to slide in a hole 22 in the centre of element 2 has a conical tip which engages in a correspondingly shaped socket/depression 23 in the end of element 3. Pin 21 is kept in engagement with the depression 23 by compression of the spring 24 that biases the pin 21 forwardly.

The tilt fail-safe mechanism is activated when a force tending to tilt distal component 3 relative to proximal component 2 is sufficient to cause the tip 25 to slide up the angled side 26 of the depression 23, further compressing the spring 24. The magnitude of the force required to do this can be controlled by the amount of the compression of the spring 24. This in turn is controlled by the element 27 which is a threaded fit in the hole 22 and whose position can be changed by a screw adjustment. Once the tip 25 has been pushed out of the depression 23 it drops into a circular groove 28. Further angulation of proximal component 2 and/or distal component 3 is prevented by the physical limit imposed by the body 13.

Figure 7:
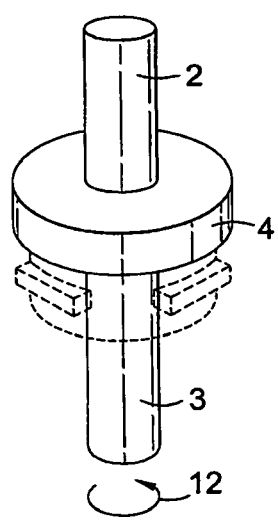
FIG. 7 is a view similar to FIG. 1 but with the parts of the attachment responsible for bending articulation omitted to highlight the rotation mechanism part.

An overall view of the clutch/axial rotation mechanism unit 4 is shown in FIG. 7. It couples (partial) axial rotation 12 of the distal component 3 with the proximal component 2 until the applied torque exceeds a safe level, at which point the two are uncoupled and the proximal component rotation is then able to occur.

Figure 8:
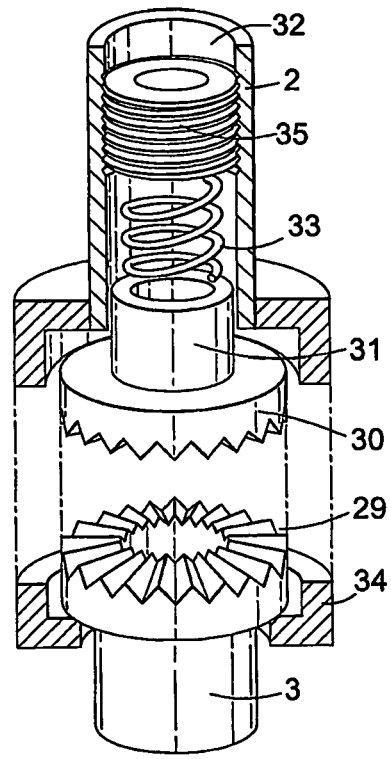
FIG. 8 is a cut-away view corresponding to FIG. 7 and showing the construction of the clutch mechanism that rotationally couples the proximal component for axial rotation with the distal component until excessive torque is applied.

The construction of the clutch mechanism 4 is shown diagrammatically in FIG. 8. The radially serrated face 29 on the end of distal component 3 engages with a similarly serrated face 30 on the end of a cylindrical-shaped pin 31. Pin 31 is free to slide inside the hole 32 in the centre of proximal component 2 but is prevented from rotating relative to it by a key (not shown) which engages in longitudinal grooves in the outer wall of element 31 and in the inner wall of element 2. The faces 29 and 30 are held in engagement by the spring 33 exerting a distal force on element 30 while the outer case of the mechanism 34 exerts a proximal force on element 3. Compression of the spring 33 is controlled by screw adjustment of the cylindrical element 35 which is a threaded fit within the hole 32.

The axial rotation fail-safe mechanism triggered when a torque tending to rotate distal component 3 relative to proximal component 2 is sufficient to cause the sloping faces of the serrations of faces 29 and 30 to slide past one another, further compressing the spring 33.

Figure 9:
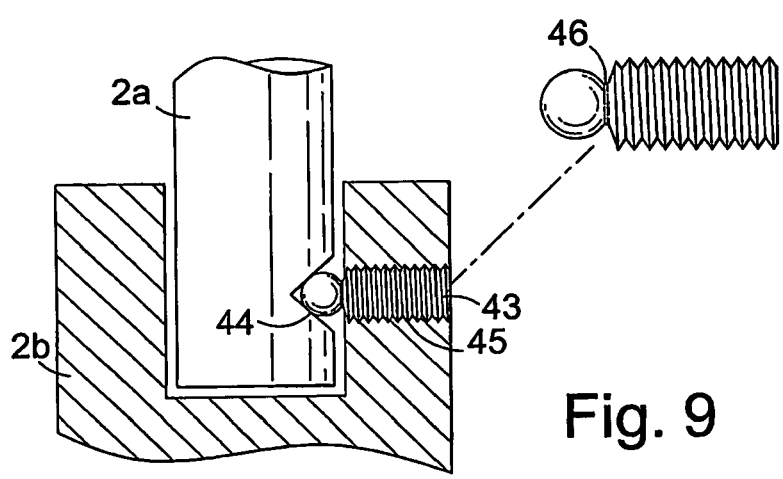
FIG. 9 is a schematic long sectional view of a modified embodiment of the attachment device in which the proximal component is itself split into proximal and distal parts coupled together via a shear pin.

As a further facility to failsafe against excessive forces (specifically tensile forces) the proximal component is suitably subdivided into proximal and distal parts 2a, 2b coupled together by a shear pin. Referring to FIG. 9, the proximal part 2a of the proximal component 2 that mounts in the bone is coupled to the distal part 2b by extending into a socket in the distal part 2b and is held in place by shear pin 43 that extends through the wall of the socket in the distal part 2b and into cooperative engagement with a groove 44 formed in a lateral face of the proximal part 2a of proximal component 2. The shear pin 43 is threaded to enable it to be adjusted in its extent of projection into the socket and hence into the groove 44 of the proximal part 2a of proximal component 2 to lock the latter in place.

At the end of the shear pin 43 which co-operatively engages with the groove 44 there is provided a weakened neck zone 46 whereby that end of the shear pin 43 may break off when excessive tensile/pulling force is applied to the joint distracting the joint. Accordingly, the articulation of the attachment device of the present invention will generally protect the patient's residual limb from harm when excess torsional or lateral forces are applied to it and the shear pin coupling will protect the patient's residual limb from excessive tensile forces on the prosthetic limb.

The shear pin coupling usefully doubles as means for daily mounting and demounting of the prosthesis from the patient's residual limb as well as providing tensile failsafe, simply by demounting the shear pin 43 by unscrewing it from engagement with groove 44.

The invention claimed is:

1. A failsafe apparatus for attaching a prosthetic limb to a transcutaneous bone implant attached through the skin directly to the bone of a patient, wherein forces of various levels may be applied to the limb, including a bending force urging the limb toward tilting, the failsafe apparatus comprising:

a proximal component to mount to a bone implant;

a distal component to mount to a prosthetic limb; and a disengageable connector for coupling the proximal and distal components and for preventing said bending force at a level greater than a predetermined threshold safe level from being transmitted by the limb to the bone implant, including resilient means for (a) coupling and holding the components in a fixed angle relationship to each other for normal use of the prosthetic limb when the limb is subject to an applied bending force less than said predetermined threshold safe level, the effect of the resilient means in holding the components in fixed relationship to each other being opposed by any said applied bending force, and (b) disengaging the disengageable connector automatically only when the bending force is greater than said predetermined threshold safe level, thereby being sufficient to overcome the maximum effect of the resilient means, and by disengagement for permitting tilting of the components away from said fixed angel relationship for a level of bending force greater than said predetermined threshold safe level, thereby providing failsafe protection of the bone implant from the effect of said bending force at a level greater that said predetermined threshold safe level.

2. An apparatus as claimed in claim 1, wherein the disengageable connector couples together the proximal and distal components so that one is in a fixed angle relation to the other in said normal use, but with freedom to articulate away from the fixed angle relation when, in use, a bending force is applied to the prosthetic limb only when the force exceeds said threshold level.

3. An apparatus as claimed in claim 2, wherein the apparatus with disengageable connector has a resilient biasing means whereby the disengageable connector is resiliently biased to the coupled state and whereof the biasing force applied to the disengageable connector by the resilient biasing means in use determines the threshold level of bending force on the prosthetic limb that will cause disengagement of the disengageable connector.

4. An apparatus as claimed in claim 3, wherein the disengageable connector comprises a pin mounted to one of the proximal and distal components and co-operating with a socket in the other of the proximal and distal components.

5. An apparatus as claimed in claim 4, wherein the pin is mounted to be movable back and forth axially of the component to which it is mounted and is biased forwardly.

6. An apparatus as claimed in claim 4, wherein the pin has a pointed or domed tip and the socket is of a corresponding concave shape whereby a bending force applied to the prosthetic limb in use will cause the tip of the pin to ride outwardly up the socket wall.

7. An apparatus as claimed in claim 6, wherein the shape of the tip is domed or substantially conical to facilitate disengagement of the disengageable connector from whichever radial orientation the bending force is applied.

8. An apparatus as claimed in claim 2, wherein the disengageable connector is configured to allow gyrating articulation or universal articulation, substantially in the manner of a ball joint, when it disengages.

9. An apparatus as claimed in claim 2, wherein the disengageable connector comprises a T-shaped formation at the end of one or both of the proximal and distal components that are adjacent each other, the head of the or each T-shaped formation being curved/arcuate to facilitate tilting of one component relative to the other.

10. An apparatus as claimed in claim 9, including a coupling body, wherein the T-shaped formations are accommodated in the coupling body, or a further coupling body, to tilt within the coupling body.

11. An apparatus as claimed in claim 10, wherein the coupling body has slots therethrough, through each of which a respective end of a head of a T-shaped formation extends and whereby the end may protrude to a greater or lesser extent as the component tilts, whereby the coupling body provides a captive articulated joint with a restricted degree of tilting freedom of movement.

12. An apparatus as claimed in claim 10, wherein one T-shaped formation is oriented in the coupling body with its head substantially orthogonal to the head of the other, whereby through tilting of each relative to the other an approximately universal or gyrating articulation may be achieved.

13. A failsafe apparatus for attaching a prosthetic limb to the bone of a patient, wherein a force may be applied to the limb urging the limb toward bending or rotational articulation, the failsafe apparatus comprising:
   a proximal component to mount to a bone implant;
   a distal component to mount to a prosthetic limb;
   a coupling body coupling the proximal and distal components moveably with respect to each other in bending and axial rotational articulation around an axis of the limb, said coupling body including
      a resilient biasing means for applying a predetermined biasing force holding the components in a fixed relationship to each other for normal use of the prosthetic limb, the effect of said biasing force being opposed by any said force applied to the limb urging the limb toward said at least one bending or rotational articulation, and only when said force applied to the limb exceeds a predetermined threshold safe level and thereby becomes sufficient to overcome the effect of the biasing force, the resilient biasing means allows the components automatically to move in said at least one bending or axial rotational articulation, thereby providing failsafe protection of the limb from excessive force applied to the limb, said resilient biasing means including
      a clutch-like mechanism having opposing sets of co-operating clutch teeth wherein the teeth are substantially symmetrical in profile whereby the clutch-like mechanism may be disengaged in either rotational direction of torque, clock-wise or anti-clockwise, applied to the prosthetic limb and
      a pin mounted to one of the proximal and distal components and co-operating with a socket of a corresponding concave shape in the other of the proximal and distal components, whereby a bending force applied to the prosthetic limb in use will cause the tip of the pin to ride outwardly up the socket wall in the direction controlled by the bending force.

14. A failsafe apparatus for attaching a prosthetic limb to a transcutaneous bone implant attached through the skin directly to the bone of a patient, wherein a force may be applied to the limb urging the limb toward tilting and/or rotational articulation, the failsafe apparatus comprising:
   a proximal component to mount to a bone implant;
   a distal component to mount to a prosthetic limb;
   a coupling body coupling the proximal and distal components moveably with respect to each other in a tilting and an axial rotational articulation, said coupling body including
      a mechanism for holding said proximal and distal components in relation to each other so that the components can be engaged and can be disengaged, wherein when the components are engaged, one component is in a fixed relation to the other, preventing said tilting and axial rotation, and wherein when the components are disengaged, said tilting and/or axial rotation is allowed, said coupling body including
      a resilient biasing means for applying a biasing force holding one of the components engaged with the other component for normal use of the prosthetic limb subject to an applied force less than a predetermined threshold safe level, the effect of said biasing force being opposed by any said force applied to the limb urging the limb toward said tilting and/or rotational articulation, and only when said force applied to the limb exceeds a said threshold safe level and thereby becomes sufficient to overcome the effect of the biasing force, the resilient biasing means allows the components automatically to become disengaged and thereby to move in said tilting and/or axial rotational articulation, thereby providing failsafe protection of the limb from excessive force applied to the limb.

* * * * *